United States Patent [19]

Ostermaier

[11] Patent Number: 4,521,628
[45] Date of Patent: Jun. 4, 1985

[54] RECOVERY OF ARYLBORANES

[75] Inventor: John J. Ostermaier, Orange, Tex.

[73] Assignee: E. I. Du Pont De Nemours and Company, Wilmington, Del.

[21] Appl. No.: 512,686

[22] Filed: Jul. 11, 1983

[51] Int. Cl.$^3$ .............................................. C07F 5/02
[52] U.S. Cl. ...................................................... 568/1
[58] Field of Search ............................................ 568/1

[56] References Cited

U.S. PATENT DOCUMENTS

| 3,090,801 | 5/1963 | Washburn et al. | 260/462 |
| 4,045,495 | 8/1977 | Nazarenko et al. | 260/606.5 B |
| 4,046,815 | 9/1977 | Nazarenko | 260/606.5 B |
| 4,076,756 | 2/1978 | Nazarenko et al. | 260/606.5 B |
| 4,082,811 | 4/1978 | Shook | 568/1 |
| 4,134,923 | 1/1979 | Reimer | 568/1 |
| 4,177,215 | 12/1979 | Seidel | 260/606.5 B |
| 4,251,468 | 2/1981 | Nazarenko | 568/1 |
| 4,416,824 | 11/1983 | Reimer et al. | 568/1 X |

OTHER PUBLICATIONS

"Theory of Particulate Process", A. D. Randolph et al., Section 8.5, pp. 146-154, *Academic Press*, New York, (1971).

*Primary Examiner*—Helen M. S. Sneed

[57] ABSTRACT

Arylboranes are recovered from aqueous solutions of their basic adducts in improved yield by staged neutralization.

6 Claims, No Drawings

RECOVERY OF ARYLBORANES

BACKGROUND OF THE INVENTION

1. Field of the Invention

The present invention is directed to the recovery of arylboranes from their basic adducts. The adducts are usually dissolved in aqueous solution and the borane is obtained by neutralizing the adduct in at least two successive stages with decreasing pH in each successive stage.

2. Description of the Prior Art

Numerous processes for the preparation of organoboranes have been disclosed in the prior art including a Grignard reaction and the reaction of an alkali metal, an organohalide and an orthoborate ester.

U.S. Pat. No. 3,090,801 issued on May 21, 1963 to Washburn et al. discloses one such process for the preparation of mono, di, tri and tetrasubstituted boranes.

U.S. Pat. Nos. 4,045,495 issued on Aug. 30, 1977, 4,046,815 issued on Sept. 6, 1977 and 4,076,756 issued on Feb. 28, 1978 disclose an improved process for the preparation of triarylboranes by reacting an alkali metal such as sodium, an organohalide such as chlorobenzene and an orthoborate ester such as triisopropylorthoborate in an organic solvent and then contacting the reaction product with water to form the alkali metal adduct of the borane reaction product. The adduct solution can be further treated to remove materials which might cause degradation of the borane before the borane is recovered by neutralization of the basic adduct.

U.S. Pat. No. 4,177,215 issued on Dec. 4, 1979 describes a method for separating di and trisubstituted arylboranes by control of the pH during neutralization.

The use of multiple crystallization vessels arranged in series to effect crystal size distribution is discussed in the text Theory Of Particulate Process, A. D. Randolph et al., Section 8.5, pages 146–154, Academic Press, New York (1971). The reference does not deal with a system wherein neutralization is conducted or wherein precipitation of the product occurs.

SUMMARY OF THE INVENTION

The present invention is a process for recovery of arylboranes, particularly triarylboranes from their adducts, e.g., the alkali metal hydroxide adducts which adducts are normally dissolved in a basic aqueous solution by conducting the neutralization of the adduct in at least two successive stages wherein in the first stage up to about 90% of the adduct is neutralized to an initial pH, e.g., 8.0–8.7 and at least a portion of the remainder of the unneutralized adduct present in the solution is subsequently neutralized in a second stage to a final pH which is lower than the initial pH, e.g., about 7.8–7.0. The recovery of triarylboranes, e.g., triphenylborane is of particular interest.

The arylboranes to which the present process is particularly applicable are the triarylboranes including those having the formula of $R_3-B$ where R is an aryl or substituted aryl group having 6-12 carbon atoms, e.g., phenyl, orthotolyl, paratolyl, naphthyl, methoxy paraphenyl, para-aminophenyl, biphenyl, chlorophenyl and bromophenyl. When the arylboranes are prepared according to the more recent techniques as, for example, by the process disclosed in U.S. Pat. No. 4,046,815 issued on Sept. 6, 1977, the ratios of triarylborane, e.g., triphenylborane to the disubstituted borane, e.g., diphenylboronic acid is usually greater than 13-15:1 and the triaryl substituted borane can be readily recovered from its adduct solution. Precipitation of the disubstituted borinic acid along with the trisubstituted borane is not significant at these high ratios because the disubstituted materials remain in solution. When disubstituted boranes are present in amounts wherein coprecipitation is likely to occur, additional methods, such as the method disclosed in U.S. Pat. No. 4,177,215 issued on Dec. 4, 1979 the disclosure of which is incorporated herein by this reference, should be followed.

The present process is preferably conducted in a continuous manner. Although the number of stages wherein neutralization is accomplished can vary depending upon the material being neutralized, at least two immediately successive stages are required. As used herein, the term stage refers to a zone wherein acid is introduced usually resulting in the reduction of the pH of the material in the stage as it is driven toward neutral. Equal or varying amounts of neutralizing agent can be introduced into each stage. It is not necessary to introduce neutralizing materials into each zone in a series of zones but only those zones wherein neutralization occurs are considered stages for purposes of the present invention. Thus, a zone wherein no neutralizing material is introduced can be interposed between two stages wherein neutralization is accomplished without departing from the spirit of the present invention.

The arrangement and design of equipment to provide the stages is not critical to the present invention. In a preferred embodiment, the staging is accomplished by arranging a number of standard crystallizer vessels in series. Adduct solution can be fed to the first vessel in the series and the effluent from each vessel fed to the next vessel. Neutralizing acid can be divided and fed to each vessel in a parallel manner. Preferably a stoichiometric amount of acid is supplied to neutralize the adduct present in the feed. The stages need not be physically separated but may be identified by a plurality of locations, e.g., as in a pipe line reactor, where acid is introduced to neutralize the adduct and permitted to substantially react before the next point of introduction of the acid. Other devices should be apparent to those skilled in the art.

There are two primary benefits from staging as well as many secondary ones. The first primary benefit is that the shape of crystals obtained are more suitable for handling and separation as compared to those obtained in a single stage operating at yields above 85%. The second primary benefit is that the yield which can be obtained in multi-staged crystallization is markedly increased over that which can be obtained in single-stage crystallization without a sacrifice of product quality. Secondary benefits from this type of operation include a reduced fines content of the product which minimizes blinding of filter cloth, a reduced moisture content in the solid product which improves its drying characteristics and thereby reduces degradation of the material which can occur in the presence of water at elevated temperatures and reduced filter cake resistance which permits an increase in production rate since the solids can now be separated more rapidly from the liquid.

With regard to the system of particular interest, i.e., in the recovery of triphenylborane by neutralizing the sodium hydroxide adduct of the borane with hydrochloric acid, it has been found that in order for high yield of the triphenylborane to be achieved, the reaction should be carried out using equal molar (stoichiometric) amounts of the adduct and hydrochloric acid. However, operation in a single stage at equal molar ratios yields crystals having a needle-like structure. These crystals are fragile, difficult to filter and to dry because they retain large quantities of moisture. In order to reduce the formation of needle-like crystals it has been necessary to operate at acid to adduct levels less than the stoichiometric which operation results in a decreased yield to triphenylborane. It is believed that as the degree of supersaturation increases, the tendency to form needle-like crystals increases. Since operating a single-stage precipitation crystallizer at high yield requires operation at high supersaturation, the result is more needle-like crystals. If a plurality of neutralization zones are employed, the supersaturation can be divided between these zones and thereby form better shaped crystals.

The following Examples and Comparatives are presented to illustrate but not to restrict the present invention. Parts and percentages are by weight unless otherwise noted. Composition of the adduct solution employed in the Examples is set forth in Table I.

TABLE I

| Component | Amount (% by weight) |
|---|---|
| Monophenylborinic acid | 0.10 |
| Diphenylborinic acid | 0.25 |
| Triphenylborane | 8.5 |
| Tetraphenylborane | 0.5 |
| Sodium Hydroxide | 4.2 |
| Water | 80.0 |
| NaCl | 6.2 |

Cake moisture was determined by filtering a definite quantity of slurry through a sintered glass filter. The solid filter cake of triphenylboron was then washed with water to remove the residual mother liquor. After washing, the weight of the wet cake was determined. The wet cake was then dried at room temperature by passing dry nitrogen gas through the cake, and the dry weight determined. The amount of water in the cake was obtained by difference. The cake moisture was calculated as the ratio of water removed to the amount of dry solids recovered and is reported as grams of water per gram of solid.

Filter cake resistance was measured using the procedure described on pp. 935 to 942 of Unit Operations of Chemical Engineering, Third Edition, by W. L. McCabe and J. C. Smith. The specific cake resistance ($\alpha$) is a measure of the resistance of the cake to flow of liquid; the lower the value of $\alpha$, the more easily the material filters.

EXAMPLES AND COMPARATIVES

The apparatus employed in the Examples and Comparatives consisted of a two-vessel neutralization apparatus which could be operated as one- or two-stages. The first stage was circulating loop designed to simulate the circulation pattern in a circulating draft tube crystallizer; the volume of this stage was 2.5 l. Circulation was achieved using a screw-type agitator, and acid and adduct feeds were admitted in the vicinity of the agitator to provide good mixing. The second stage was a cylindrical vessel of 2.5 l volume which contained a draft tube and turbine-type agitator. Acid was added to the second vessel in the draft tube below the liquid surface. Slurry product from the first crystallizer overflowed by gravity to the second stage and the product from the second stage discharged to a product receiver. An aqueous solution of 7% hydrochloric acid was introduced into each stage to obtain the indicated pH. All runs were made at a crystallizer temperature of 40° C. and a hold up time of 30 minutes.

The crystallizer was charged with the adduct solution shown in Table I and circulation was established. The temperature was then raised to 40° C. by an electrical heating tape wrapped around part of the circulating loop. Acid was added continuously over a period of 30 min. to reduce the pH to the desired operating level following which adduct flow was established at the rate of 60 cc/min., and acid flow was controlled to maintain the indicated pH in the crystallizers. The overflow from the first crystallizer was fed to the second crystallizer and when overflow from the second crystallizer commenced, acid was added over a period of 1 min. to adjust the second stage pH to the indicated level. Acid flow to the second vessel was then adjusted to maintain the indicated pH in the second stage. Overflow from the second stage was collected for six hours. The solids were separated from the mother liquor and evaluated. The mother liquor was analyzed for triphenylborane to determine yield loss. The results are reported in Table II.

TABLE II

| | pH | | Cake | Specific Cake Resistance ($\alpha$) |
|---|---|---|---|---|
| | Stage I | Stage II | Moisture | ft/lb |
| Example No. | | | | |
| 1 | 8.00 | 7.05 | 0.56 | $2.9 \times 10^8$ |
| 2 | 8.18 | 7.05 | 0.56 | $2.4 \times 10^8$ |
| Comparative | | | | |
| 1 | 7.97 | 7.97 | 0.66 | $2.2 \times 10^8$ |
| 2 | 6.99 | 6.99 | 0.78 | $9.0 \times 10^8$ |

| | Yield Loss (Wt. % Triphenylborane in filtrate) | Crystal Appearance |
|---|---|---|
| Example No. | | |
| 1 | 1.4 | Granular |
| 2 | 1.7 | Granular |
| Comparative | | |
| 1 | 8.8 | Granular |
| 2 | 1.0 | Needles |

I claim:

1. A process for the recovery of arylboranes from their adducts which adducts are dissolved in a basic aqueous solution comprising neutralizing the adduct in at least two stages wherein up to about 90% of the adduct present in the solution is neutralized in the first stage to an initial pH and at least a portion of the remainder of the unneutralized adduct present in the solution is neutralized in the second stage to a final pH which is lower than the initial pH.

2. The process of claim 1 wherein the initial pH is maintained in the range of about 8.0–8.7 and the final pH is maintained in the range of about 7.8–7.0.

3. The process of claim 1 wherein 50–90% of the adduct initially present in solution is neutralized in the first stage.

4. The process of claim 3 wherein the arylborane is triphenylborane.

5. The process of claim 3 wherein the adduct is the alkali metal hydroxide adduct of triarylborane.

6. The process of claim 5 wherein the adduct is the sodium hydroxide adduct of triphenylborane.

* * * * *